(12) United States Patent
Morris

(10) Patent No.: US 8,445,723 B2
(45) Date of Patent: May 21, 2013

(54) PROCESSES FOR PRODUCING N-ALKYL (ALKYL)ACRYLAMIDES

(75) Inventor: John D. Morris, Naperville, IL (US)

(73) Assignee: Nalco Company, Naperville, IL (US)

( * ) Notice: Subject to any disclaimer, the term of this patent is extended or adjusted under 35 U.S.C. 154(b) by 806 days.

(21) Appl. No.: 12/194,267

(22) Filed: Aug. 19, 2008

(65) Prior Publication Data
US 2010/0048951 A1 Feb. 25, 2010

(51) Int. Cl.
*C07C 231/02* (2006.01)
(52) U.S. Cl.
USPC .......................................................... 564/144
(58) Field of Classification Search
USPC .......................................................... 564/144
See application file for complete search history.

(56) References Cited

U.S. PATENT DOCUMENTS

| | | | | |
|---|---|---|---|---|
| 2,311,548 | A * | 2/1943 | Jacobson et al. | 526/307.7 |
| 6,527,959 | B1 | 3/2003 | Quadir et al. | |
| 6,933,735 | B2 | 8/2005 | Zayas et al. | |
| 7,138,472 | B2 | 11/2006 | Quadir et al. | |

FOREIGN PATENT DOCUMENTS

| | | |
|---|---|---|
| DE | 3412650 | 10/1985 |
| JP | 61162519 | 7/1986 |
| SU | 239314 A | 7/1969 |
| WO | 2006045919 | 5/2006 |
| WO | 2007147652 | 12/2007 |
| WO | 2007147653 | 12/2007 |
| WO | 2008074523 | 6/2008 |

OTHER PUBLICATIONS

Iwakura et al, Journal of Organic Chemistry, vol. 32, No. 2, pp. 440-443, 1967.*
Drobnik J. et. al.; "Enzymatic Cleavage of Side Chains of Synthetic Water-Soluble Polymers," Macromolecular Chemistry and Physics, vol. 177, Jan. 1, 1976, pp. 2833-2848, XP-000943422.
Yoshio Iwakura, Fujio Toda, Hideaki Suzuki, "Synthesis and Polymerization of N-[1-(1-Substituted-2-oxopropyl)] acrylamides and—methacrylamides. Copolymerization of These Monomers with Styrene and Substituent Effects", Journal of Polymer Science, Part A-1, vol. 5, No. 7, Jul. 1967, pp. 1599-1607, XP-002567338.

* cited by examiner

*Primary Examiner* — Shailendra Kumar
(74) *Attorney, Agent, or Firm* — Edward O. Yonter; Andrew D. Sorensen

(57) ABSTRACT

Methods of producing the N-alkyl(alkyl)acrylamides. In a general embodiment, the present disclosure provides a method of producing an N-alkyl (alkyl)acrylamide comprising providing an aqueous solution comprising an N-alkyl amine and adding to the aqueous solution a base and an (alkyl)acrylic anhydride to form a precipitated N-alkyl(alkyl) acrylamide.

8 Claims, No Drawings

PROCESSES FOR PRODUCING N-ALKYL (ALKYL)ACRYLAMIDES

BACKGROUND

The present disclosure relates generally to N-alkyl(alkyl) acrylamides. More specifically, the present disclosure relates to methods of producing N-alkyl (alkyl)acrylamides and using the N-alkyl(alkyl)acrylamides.

Anhydrides are relatively reactive in the presence of nucleophiles such as amines, hydroxides, alkoxides, etc. The reactions of acrylic anhydrides and (meth)acrylic anhydrides with a nucleophile such as an amine produces the corresponding acrylic or (meth)acrylic acid, and the subsequent nucleophilic addition product as the other monomer. The resulting N-alkyl(alkyl)acrylamides can be useful as building blocks for polymeric gas hydrate inhibitors. Nevertheless, these reactions can have associated problems related to purification of the final products and the control over side reactions.

SUMMARY

The present disclosure relates to methods of producing N-alkyl (alkyl)acrylamides. In a general embodiment, the present disclosure provides a method of producing an N-alkyl (alkyl)acrylamide. The method comprises providing an aqueous solution comprising an N-alkyl amine and adding to the aqueous solution a base and an (alkyl)acrylic anhydride to form a precipitated N-alkyl(alkyl)acrylamide.

In an embodiment, the method further comprises filtering the aqueous solution to remove the precipitated N-alkyl (alkyl)acrylamide from the aqueous solution. The precipitated N-alkyl(alkyl)acrylamide that was filtered can further be washed to remove any contaminant from the N-alkyl (alkyl)acrylamide.

In an embodiment, the removed contaminant is substantially an (alkyl)acrylic acid salt coproduct.

In an embodiment, the (alkyl)acrylic anhydride and the base are added to the aqueous solution at a temperature of below about 30° C.

In an embodiment, the N-alkyl amine comprises a compound having the formula $H_2N(R)$, wherein R is an alkyl group such as a linear hydrocarbon of 1 to 8 carbon units or a branched hydrocarbon of 1 to 8 carbon units.

In an embodiment, the alkyl group that comprises the R includes a heteroatom that is oxygen, sulfur or a combination thereof.

In an embodiment, the N-alkyl amine is methylamine, ethylamine, 1-propylamine, 2-propylamine(isopropylamine), 1-butylamine, 2-butylamine, 1-methyl-1-propylamine, 2-methyl-1-propylamine or a combination thereof.

In an embodiment, the (alkyl)acrylic anhydride is a di(alkyl)acrylic anhydride.

In an embodiment, the base is sodium hydroxide, potassium hydroxide, ammonium hydroxide or a combination thereof.

In an embodiment, the precipitated N-alkyl(alkyl)acrylamide has the following structure:

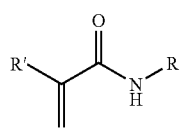

wherein R is selected from the group of a linear hydrocarbon of 1 to 8 carbon units and a branched hydrocarbon of 1 to 8 carbon units, and R' is selected from the group consisting of hydrogen and methyl.

In an embodiment, R' is methyl and R is isopropyl.

In another embodiment, the present disclosure provides a method of producing an N-alkyl(meth)acrylamide. The method comprises providing an aqueous solution comprising an N-alkyl amine and adding to the aqueous solution a base and an amount of a (meth)acrylic anhydride to form a precipitated N-alkyl (meth)acrylamide.

In an embodiment, the method further comprises filtering the aqueous solution to remove the precipitated N-alkyl (meth)acrylamide from the aqueous solution.

In an embodiment, the method further comprises washing the precipitated N-alkyl(meth)acrylamide that was filtered to remove any contaminant from the N-alkyl(meth)acrylamide.

An advantage of the present disclosure is to provide an improved method of making N-alkyl(alkyl)acrylamides.

Another advantage of the present disclosure is to provide an improved method of making N-alkyl(meth)acrylamides.

Additional features and advantages are described herein, and will be apparent from the following Detailed Description.

DETAILED DESCRIPTION

The present disclosure relates to methods of producing N-alkyl (alkyl)acrylamides and using the N-alkyl(alkyl)acrylamides. In a general embodiment, an aqueous process is used to produce N-alkyl(alkyl)acrylamides from the reaction of an N-alkyl amine with an (alkyl)acrylic anhydride (e.g. acrylic anhydride, (meth)acrylic anhydride). The N-alkyl(alkyl) acrylamides produced are of suitable quality for use in subsequent free radical polymerization reactions and other similar chemistries.

Some advantages of the methods of making N-alkyl(alkylacrylamides in embodiments of the present disclosure over previous procedures described in the literature relate to the ease of purification of the method and the control over side reactions. In addition, the non-volatility of the solvent (e.g. water) provides another advantage during the reactions. The reactions can be performed at relatively low temperatures and thus the desired addition product is favored over other potential side-reactions such as Michael-type reactions that might occur between amines and acrylics at elevated temperatures.

As used herein, "alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, and the like.

In a general embodiment, the present disclosure provides a method of producing an N-alkyl(alkyl)acrylamide. The method comprises providing an aqueous solution comprising an N-alkyl amine and adding to the aqueous solution a base and an (alkyl)acrylic anhydride. The base and the (alkyl) acrylic anhydride can be added to the aqueous solution while stirring the aqueous solution. The aqueous solution of a base and the (alkyl)acrylic anhydride can be added sequentially or simultaneously. Alternatively, an aqueous solution of base and (alkyl)acrylic anhydride can be prepared and then the N-alkyl amine added. The produced N-alkyl(alkyl)acrylamide monomer, formed by reaction between the amine and the anhydride, can precipitate from the reaction mixture as a relatively pure product.

In an embodiment, an approximate equimolar amount of both the (alkyl)acrylic anhydride and a base can be added to the aqueous solution. The base can any suitable base such as, for example, sodium hydroxide, potassium hydroxide, ammonium hydroxide and the like. The (alkyl)acrylic anhydride and the base can be added to and/or mixed in the aqueous solution at a temperature of below about 30° C. In another embodiment, the (alkyl)acrylic anhydride and the base is added to and/or mixed in the aqueous solution at a temperature ranging from about 20° C. to about 30° C.

In an embodiment, the method further comprises filtering the aqueous solution to remove the precipitated N-alkyl (alkyl)acrylamide from the aqueous solution. The method can further comprise washing the precipitated N-alkyl (alkyl) acrylamide that was filtered to remove any contaminant from the N-alkyl (alkyl)acrylamide. For example, the solid/precipitated product can be filtered and washed with water to remove any (alkyl)acrylic acid salt coproduct contaminating the product.

The (alkyl)acrylic anhydride can be a di(alkyl)acrylic anhydride of formula

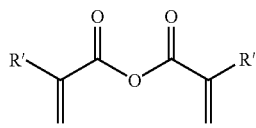

where R' is 11 or a linear hydrocarbon of 1 to 8 carbon atoms or a branched hydrocarbon of 1 to 8 carbon atoms. In a preferred embodiment, the (alkyl)acrylic anhydride is (meth) acrylic anhydride (R' is H or methyl) and the final precipitated product is N-alkyl(meth)acrylamide. The methacrylic anhydride raw material for the N-alkyl(alkyl)acrylamide monomer is commercially available or can be made using any of a number of known processes.

In an embodiment, the N-alkyl amine comprises a compound having the formula $H_2N(R)$, wherein R is an alkyl group such as a linear hydrocarbon of 1 to 8 carbon units or a branched hydrocarbon of 1 to 8 carbon units. It should be appreciated that cyclic alkyl groups are a subset of the group of branched hydrocarbons. The alkyl group that comprises the R can include a heteroatom which can be oxygen and/or sulfur as long as the number of carbon atoms remains within the range of 1 to 8. In an embodiment, the N-alkyl amine can be methylamine, ethylamine, 1-propylamine, 2-propylamine, 1-butylamine, 2-butylamine, 1-methyl-1-propylamine, 2-methyl-1-propylamine or a combination thereof.

In an embodiment, the N-alkyl(alkyl)acrylamide has the following structure:

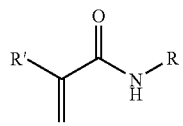

wherein R is selected from the group consisting of a linear hydrocarbon of 1 to 8 carbon units and a branched hydrocarbon of 1 to 8 carbon units, and R' is selected from the group consisting of hydrogen and methyl. In an embodiment, R' is methyl and R is isopropyl.

In another embodiment, the present disclosure provides a method of producing an N-alkyl(meth)acrylamide. The method comprises providing an aqueous solution comprising an N-alkyl amine and adding to the aqueous solution a base and an amount of a (meth)acrylic anhydride to form a precipitated N-alkyl (meth)acrylamide. The method can further comprise filtering the aqueous solution to remove the precipitated N-alkyl(meth)acrylamide from the aqueous solution and washing the precipitated N-alkyl(meth)acrylamide that was filtered to remove any contaminant from the N-alkyl (meth)acrylamide.

EXAMPLES

By way of example and not limitation, the following examples are illustrative of various embodiments of the present disclosure and further illustrate experimental testing conducted with the N-alkyl(alkyl)acrylamides in accordance with embodiments of the present disclosure.

Example 1

The following experiment utilized aqueous reaction conditions to produce N-isopropyl methacrylamide (IPMA):

32 grams of water was added to a 250 mL, three-necked resin flask equipped with a mechanical stirrer, condenser and thermocouple. The water was cooled to 5-9° C. via an ice bath. 6 grams of isopropylamine was slowly added to the cooled water while mixing.

The following components were added to the cooled, stirring isopropylamine solution separately and simultaneously via two separate syringe pumps: 1) methacrylic anhydride (16.53 g of 94% purity) and 2) a 50 wt. % aqueous solution of sodium hydroxide (8.12 g). The methacrylic anhydride and sodium hydroxide solution were each added over a one hour period while keeping the reaction temperature below 30° C. During this time, a precipitate formed in the reaction mixture. After all of the reagents were added, the reaction mixture was allowed to stir for one additional hour, and then the reactor contents were filtered. After drying the recovered solid under vacuum, 10.7 g product (LPMA) was obtained. Nuclear magnetic resonance (NMR) analysis revealed a product comprised of 93% IPMA, 4% water, and 3% impurities.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of producing an N-alkyl (alkyl)acrylamide, the method comprising:
   providing an aqueous solution comprising isopropylamine; and
   adding to the aqueous solution a base and an amount of methacrylic anhydride to form a precipitated N-alkyl (alkyl)acrylamide,
   wherein the precipitated N-alkyl (alkyl)acrylamide has the following structure:

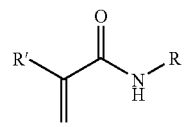

wherein R' is methyl and R is isopropyl,
   wherein the methacrylic anhydride and the base are added to the aqueous solution at a temperature of about 20 to about 30° C., and wherein an approximate equimolar amount of the methacrylic anhydride and the base is added to the aqueous solution.

2. The method of claim 1 further comprising filtering the aqueous solution to remove the precipitated N-alkyl (alkyl) acrylamide from the aqueous solution.

3. The method of claim 1, wherein the base is selected from the group consisting of sodium hydroxide, potassium hydroxide, ammonium hydroxide and combinations thereof.

4. The method of claim 2 further comprising washing the precipitated N-alkyl (alkyl)acrylamide that was filtered to remove any contaminant from the N-alkyl (alkyl)acrylamide.

5. The method of claim 1 wherein the base is aqueous sodium hydroxide.

6. The method of claim 5 wherein the methacrylic anhydride and the aqueous sodium hydroxide are added simultaneously to the aqueous solution of isopropylamine.

7. The method of claim 2, further comprising drying under vacuum the precipitated and filtered N-alkyl (alkyl)acrylamide.

8. The method of claim 7, wherein the precipitated, filtered, and dried N-alkyl (alkyl)acrylamide under nuclear magnetic resonance (NMR) analysis reveals a product comprising of 93% N-isopropyl methacrylamide, 4% water, and 3% impurities.

* * * * *